United States Patent
Lee et al.

(10) Patent No.: US 7,627,450 B2
(45) Date of Patent: Dec. 1, 2009

(54) MOVEMENT DISTANCE MEASURING APPARATUS AND METHOD

(75) Inventors: Jae-Myeon Lee, Yongin-si (KR); Hyun-Su Hong, Seongnam-si (KR); Chan-Gook Park, Seoul (KR); Jin-Won Kim, Seoul (KR); Kyong-Ha Park, Suwon-si (KR); Ji-Heon Oh, Yongin-si (KR)

(73) Assignees: Samsung Electronics Co., Ltd., Suwon, Gyeonggi-do (KR); Seoul National University Industry Foundation, Seoul (KR)

( * ) Notice: Subject to any disclaimer, the term of this patent is extended or adjusted under 35 U.S.C. 154(b) by 75 days.

(21) Appl. No.: 11/932,105

(22) Filed: Oct. 31, 2007

(65) Prior Publication Data

US 2008/0105065 A1    May 8, 2008

(30) Foreign Application Priority Data

Oct. 31, 2006    (KR) .................... 10-2006-0106916

(51) Int. Cl.
*G01C 22/00* (2006.01)
*G01P 15/00* (2006.01)

(52) U.S. Cl. ..................................... 702/158; 702/141
(58) Field of Classification Search .......... 702/141–142, 702/149, 158, 160; 701/217; 340/438; 73/146
See application file for complete search history.

(56) References Cited

U.S. PATENT DOCUMENTS

| 5,724,265 A | * | 3/1998 | Hutchings | .................... 702/141 |
| 6,571,193 B1 | * | 5/2003 | Unuma et al. | ................ 702/141 |

FOREIGN PATENT DOCUMENTS

| JP | 2000-241193 A | 9/2000 |
| KR | 10-2006-0083753 A | 7/2006 |
| KR | 10-2006-0090913 A | 8/2006 |

* cited by examiner

*Primary Examiner*—John H Le
(74) *Attorney, Agent, or Firm*—Jefferson IP Law, LLP (57) ABSTRACT

An apparatus and method for determining a location of a movement distance measuring apparatus are provided. The apparatus and method determine whether the movement distance measuring apparatus is mounted at the waist of a pedestrian or is located in a pocket and uses a different step length estimation algorithm, e.g. a different step length estimation parameter coefficient, corresponding to the determined mounting position. The determination of whether the movement distance measuring apparatus is mounted to the waist of a pedestrian or is located in a pocket is performed on the basis of a gyro sensor.

9 Claims, 6 Drawing Sheets

SQUARE SUM OF OUTPUT OF AN ACCELEROMETER

FIG.5

SQUARE SUM OF OUTPUT OF A GYRO SENSOR

MOVEMENT DISTANCE MEASURING APPARATUS AND METHOD

PRIORITY

This application claims the benefit under 35 U.S.C. §119(a) of a Korean patent application filed in the Korean Industrial Property Office on Oct. 31, 2006 and assigned Serial No. 2006-106916, the entire disclosure of which is hereby incorporated by reference.

JOINT RESEARCH AGREEMENT

The claimed invention was made by, on behalf of, and/or in connection with one or more of the following parties to a joint research agreement: Samsung Electronics Co. Ltd. and Seoul National University Industry Foundation. The agreement was in effect on and before the date the claimed invention was made, and the claimed invention was made as a result of activities undertaken within the scope of the agreement.

BACKGROUND OF THE INVENTION

1. Field of the Invention

The present invention relates to a movement distance measuring apparatus. More particularly, the present invention relates to a movement distance measuring apparatus mounted to a portable terminal.

2. Description of the Related Art

In recent years, as interest in personal health has increased, apparatuses that measure movement by determining the number of steps or by measuring movement distances have been developed. The apparatuses are occasionally mounted to mobile communication terminals which are typically carried by their users.

Figure 1A:
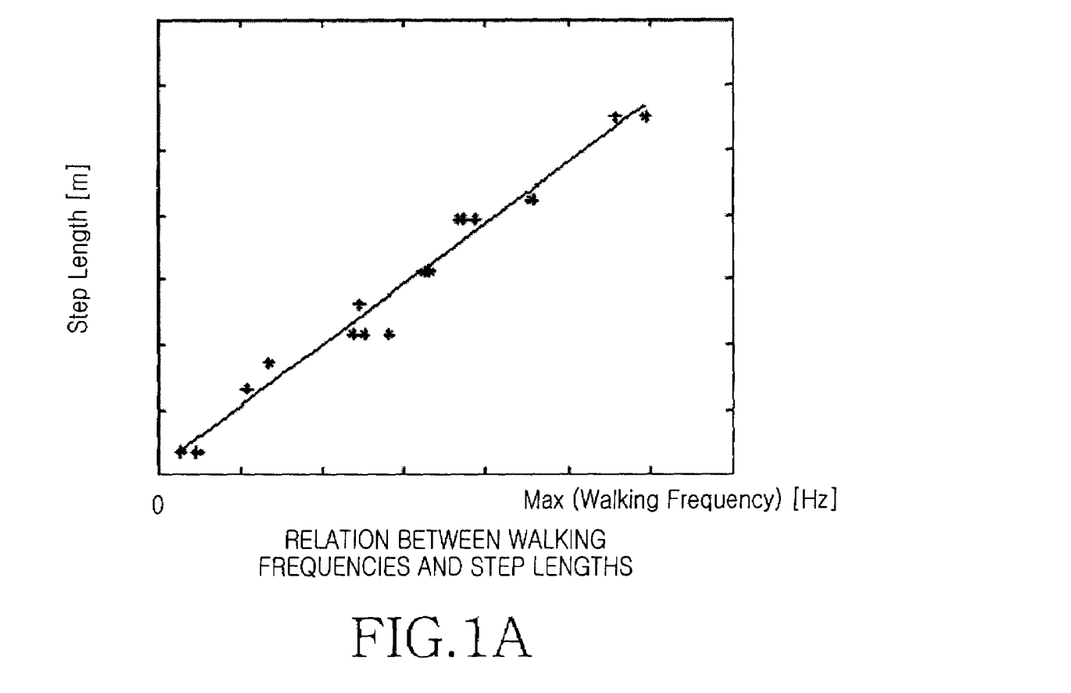
FIG. 1A is a view illustrating a relation between step lengths and walking frequencies.
Figure 1B:
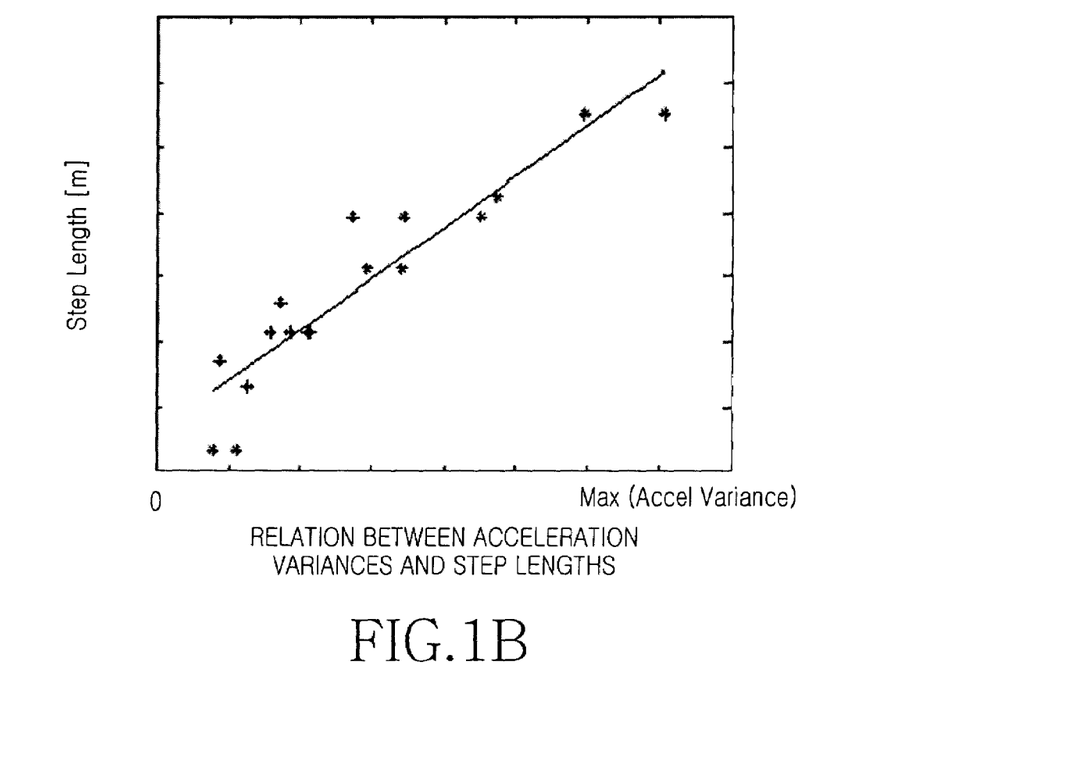
FIG. 1B is a view illustrating a relation between step lengths and acceleration variances.

To estimate a step length of a pedestrian, such a measuring apparatus uses a walking frequency and an acceleration variance that reflect the characteristics of a step length change according to a step pattern. FIG. 1A is a view illustrating a relation between step lengths and walking frequencies, and FIG. 1B is a view illustrating a relation between step lengths and acceleration variances. Referring to FIGS. 1A and 1B, it can be seen that the step lengths have linear relations with the walking frequencies and the acceleration variances. Therefore, a step length can be represented by a linear combination of the two parameters of walking frequency and acceleration variance as in equation (1) below.

$$\text{Step length} = a_1 WF + a_2 AV + b \quad (1)$$

In equation (1), $a_1$ and $a_2$ are respectively weights of a walking frequency and an acceleration variance, b is a constant term, WF is a walking frequency, and AV is an acceleration variance.

Therefore, since a walking frequency and a variance value of an accelerometer output when one step is generated can be calculated, the total movement distance can be calculated as in Equation (2) below by summating step lengths when several steps are generated.

$$\text{Movement distance} = \sum_{i=1}^{n} (a_1 WF + a_2 AV + b)_i \quad (2)$$

In equation (2), n is the number of detected steps, and $a_1$, $a_2$, and b are weights in a linear combination of a walking frequency and an acceleration variance and are calculated by a linear regression.

Figure 2:
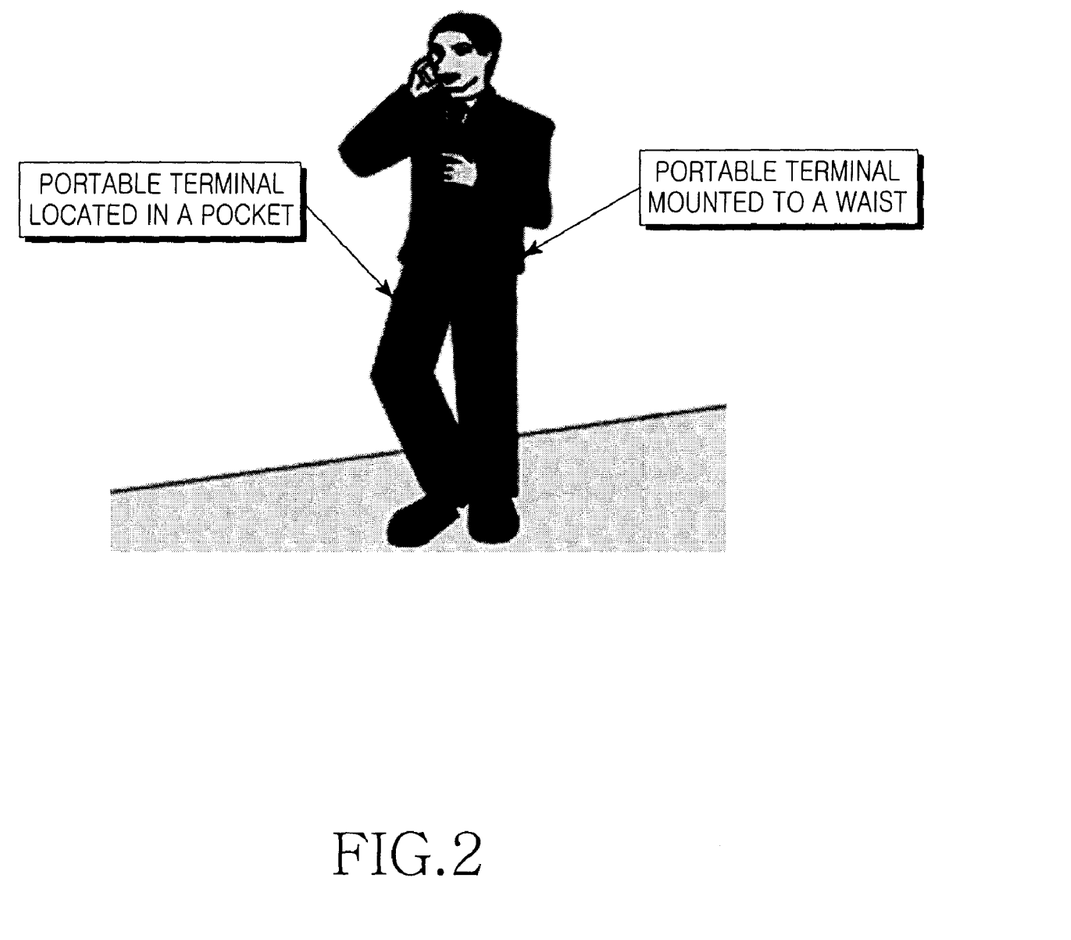
FIG. 2 is a view illustrating positions where a portable terminal including a movement distance measuring apparatus can be mounted.

As the use of portable terminals has grown, a user will occasionally mount a movement distance measuring apparatus to the portable terminal for convenience. However, in the case in which the portable terminal including the movement distance measuring apparatus is mounted at the waist of the user or is located in the user's pocket as illustrated in FIG. 2, $a_1$, $a_2$, and b, which are step length estimation parameters, are different. Accordingly, a step length estimation error is generated due to the mounting position. Therefore, a method for recognizing a mounting position so as to use a parameter coefficient suitable for the mounting position of the movement distance measuring apparatus is necessary.

That is, a conventional movement distance measuring apparatus does not address a change of an algorithm that is necessary according to a mounting position of the movement distance measuring apparatus. Because the conventional movement distance measuring apparatus cannot discriminate between mounting positions, an error becomes large and the measurement can not be properly performed since the movement distance and the movement are calculated by the same algorithm.

SUMMARY OF THE INVENTION

Accordingly, the present invention has been made to address the above-mentioned problems and/or disadvantages and to provide at least the advantages described below. Accordingly, an aspect of the present invention is to provide a movement distance measuring apparatus and a method which can accurately detect a step length, considering the mounting position of the movement distance measuring apparatus.

In accordance with an aspect of the present invention, a movement distance measuring apparatus is provided. The apparatus includes an accelerometer for detecting and outputting an acceleration signal of at least one axis, a gyro sensor for detecting and outputting an angular speed signal of at least one axis, a step detection unit for determining whether a step is detected on the basis of the output signals of the accelerometer and the gyro sensor, a mounting position determination unit for determining that the movement distance measuring apparatus is located in a pocket of a user if a step is detected on the basis of both the output signal of the accelerometer and the output of the gyro sensor and for determining that the movement distance measuring apparatus is located at the waist of a pedestrian if a step is detected on the basis of only the output signal of the accelerometer and a step length estimation unit for using a different step length estimation algorithm corresponding to the mounting position of the movement distance measuring apparatus.

In accordance with another aspect of the present invention, a movement distance measuring method of a movement distance measuring apparatus including an accelerometer for detecting and outputting an acceleration signal of at least one axis, and a gyro sensor for detecting and outputting an angular speed signal of at least one axis is provided. The method includes determining whether a step is detected on the basis of output signals of the accelerometer and the gyro sensor, determining that the movement distance measuring apparatus is located in a pocket of a user if a step is detected on the basis of both the output signal of the accelerometer and the output of the gyro sensor, determining that the movement distance measuring apparatus is located at the waist of the user if a step is detected on the basis of only the output signal of the accelerometer and using a different step length estimation algorithm according g to the mounting position of the movement distance measuring apparatus.

BRIEF DESCRIPTION OF THE DRAWINGS

The above and other aspects, features and advantages of certain exemplary embodiments of the present invention will be more apparent from the following detailed description taken in conjunction with the accompanying drawings, in which.

Throughout the drawings, it should be noted that like reference numbers are used to depict the same or similar elements, features and structures.

DETAILED DESCRIPTION OF EXEMPLARY EMBODIMENTS

The following description with reference to the accompanying drawings is provided to assist in a comprehensive understanding of exemplary embodiments of the invention as defined by the claims and their equivalents. It includes various specific details to assist in that understanding but these are to be regarded as merely exemplary. Accordingly, those of ordinary skill in the art will recognize that various changes and modifications of the embodiments described herein can be made without departing from the scope and spirit of the invention. Also, descriptions of well-known functions and constructions are omitted for clarity and conciseness.

Exemplary embodiments of the present invention determine whether a movement distance measuring apparatus is located at the waist of a pedestrian or in a pocket, and use a different step length estimation algorithm accordingly, e.g. a different step length estimation parameter coefficient according to a mounting position of the movement distance measuring apparatus. The determination of whether the movement distance measuring apparatus is mounted at the waist of a pedestrian or is located in a pocket is performed on the basis of an output signal of a gyro sensor. The elements and the operation of a portable terminal including a movement distance measuring apparatus according to an exemplary embodiment of the present invention will be described with reference to FIG. 3.

Figure 3:
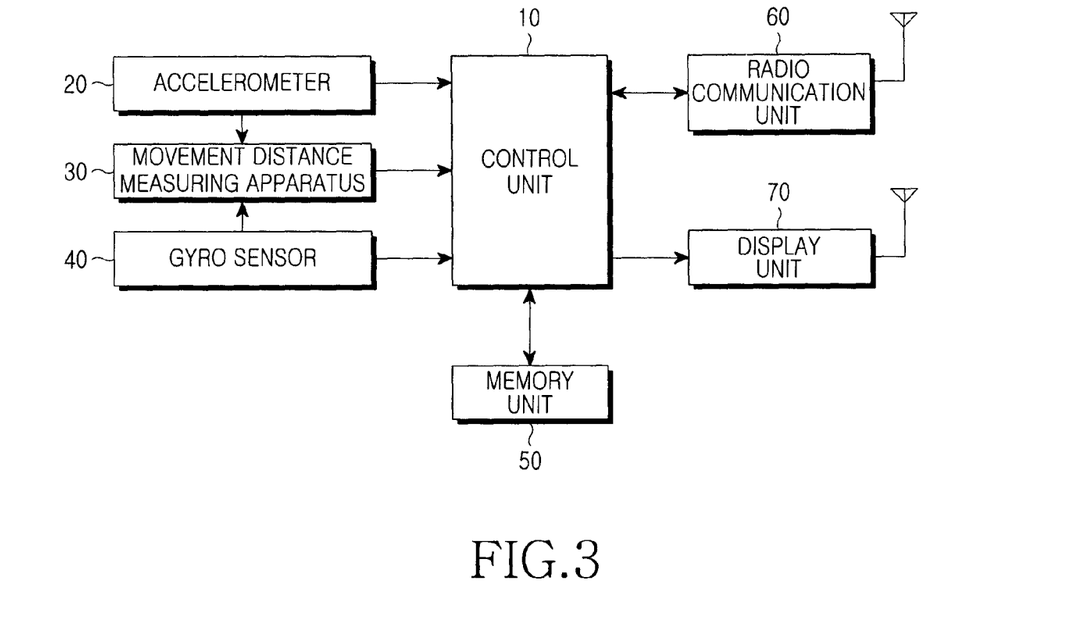
FIG. 3 is a block diagram illustrating an exemplary portable terminal of the present invention which includes a movement distance measuring apparatus.

FIG. 3 is a block diagram illustrating a portable terminal that includes a movement distance measuring apparatus according to an exemplary embodiment of the present invention. Referring to FIG. 3, the portable terminal includes a control unit 10, an accelerometer 20, a movement distance measuring apparatus 30, a gyro sensor 40, a memory unit 50, a radio communication unit 60, and a display unit 70.

The control unit 10 controls the overall operation of the portable terminal. For example, if the control unit 10 receives information such as a movement distance from the movement distance measuring apparatus 30, it can display the information on the display unit 70.

The display unit 10 may include a liquid crystal display (LCD) and may display information output from the movement distance measuring apparatus 30 according to an exemplary embodiment of the present invention. The memory unit 50 stores plurality of applications and data, and stores algorithms for functions performed by the movement distance measuring apparatus. For example, the memory unit 50 may store algorithms including a step detection algorithm, a mounting position determination algorithm, a step length estimation algorithm, and a movement measuring algorithm, according to an exemplary embodiment of the present invention. The radio communication unit 60 generally performs radio communication with a base station.

Figure 4:
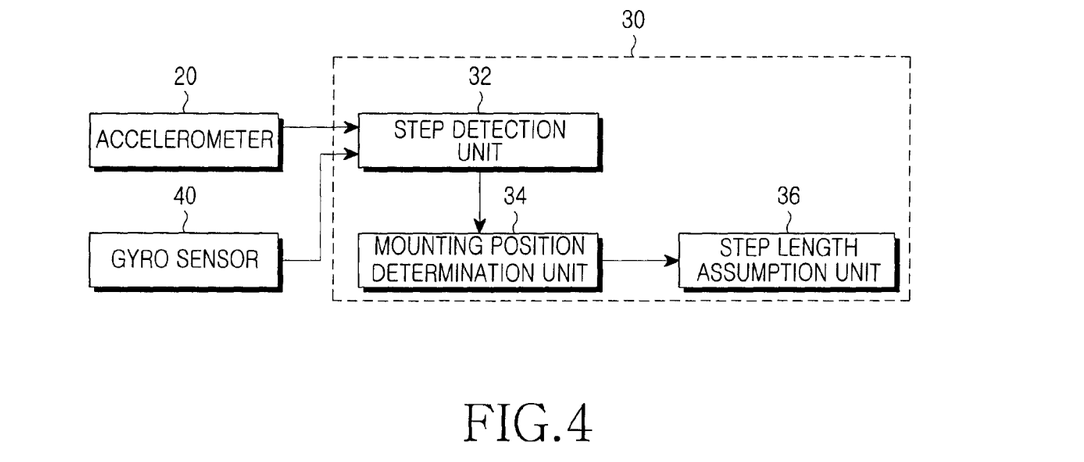
FIG. 4 is a block diagram illustrating a movement distance measuring apparatus according to an exemplary embodiment of the present invention.

The movement distance measuring apparatus 30 determines whether it is mounted at the waist of a pedestrian or is located in a pocket based on outputs of the accelerometer 20 and the gyro sensor 40. Further, the movement distance measuring apparatus 30 uses a different step length estimation parameter coefficient according to a determined mounting position of the movement distance measuring apparatus 30. The movement distance measuring apparatus will be described in more detail with reference to FIG. 4. FIG. 4 is a block diagram illustrating a movement distance measuring apparatus according to an exemplary embodiment of the present invention.

Referring to FIG. 4, the movement distance measuring apparatus 30 includes a step detection unit 32, a mounting position determination unit 34, and a step length estimation unit 36.

Outputs of the accelerometer 20 and the gyro sensor 40 are provided to the step detection unit 32. It can be noted here that in an exemplary embodiment, the accelerometer 20 and gyro sensor 40 are mounted separately from the movement distance measuring apparatus 30. However, in another exemplary embodiment, the movement distance measuring apparatus may include an accelerometer 20 and a gyro sensor 40 in the case in which the movement distance measuring apparatus is provided by itself. Furthermore, an exemplary movement distance measuring apparatus that is provided by itself may include a memory unit similar to memory unit 50 in which it may store algorithms and the like.

The accelerometer 20 may include a Micro Electro Mechanical Systems (MEMS) type accelerometer, i.e. a sub-miniature accelerometer, and may be mounted to a portable terminal or an individual navigation device such as a PDA. The accelerometer 20 can detect accelerations on at least two axes. According to an exemplary embodiment or the present invention, the accelerometer can be realized using a three-axis accelerometer or three one-axis accelerometers. The accelerometer is mounted to the portable terminal so that three axes are disposed in a lateral direction (the right or left direction), a forward direction, and a downward direction respectively. Then, although the axes are accurately disposed, since the acceleration components of walking are necessary in an exemplary embodiment, the characteristics of the accelerometer can be maintained even though the axes are deviated from the directions in a range which does not influence the acceleration signal detection. The accelerometer detects linear movements in the lateral direction, the forward direction, and the downward direction of a pedestrian, and outputs an acceleration signal corresponding to the detection result.

The gyro sensor is an angular speed sensor, and outputs an angular speed signal on a roll axis, a pitch axis, and a yaw axis, similar to the accelerometer 20.

The step detection sensor 32 detects a step using the acceleration signal output from the accelerometer 20 and the angular speed signal output from the gyro sensor 40. The accelerometer 20 and the gyro sensor 40 output different signals according to whether the portable terminal to which the movement distance measuring apparatus 30 is mounted is kept at the waist of a pedestrian or is located in a pocket.

The output signal of the accelerometer 20 represents a pattern of a step in both forward and downward directions in both cases in which the movement distance measuring apparatus 30 is mounted at the waist of a pedestrian or is located in a pocket. However, the output signal of the gyro sensor 40 represents a pattern of a step only in the case in which the movement distance measuring apparatus 30 is mounted at the waist of a pedestrian. Further, it can be seen that in the output signal of the gyro sensor 40, the roll rate and the pitch rate reflect a pattern of a step better than the yaw rate.

However, the portable terminal may be located in a pocket of a pedestrian, since the mounting position is not fixed, and it is necessary to recognize the mounting position, even when the portable terminal is mounted in any direction.

Therefore, exemplary embodiments of the present invention use a signal obtained by squaring the signals of the three axes, which are output from the accelerometer 20 and the gyro sensor 40, summating the resultant square values and removing noise included in the signal and error components by applying a sliding window summation and a low-pass filtering. In an exemplary embodiment, the sliding window summation method is a signal processing method adding the acceleration values in a window section by moving a window with respect to the time axis.

Figure 5:
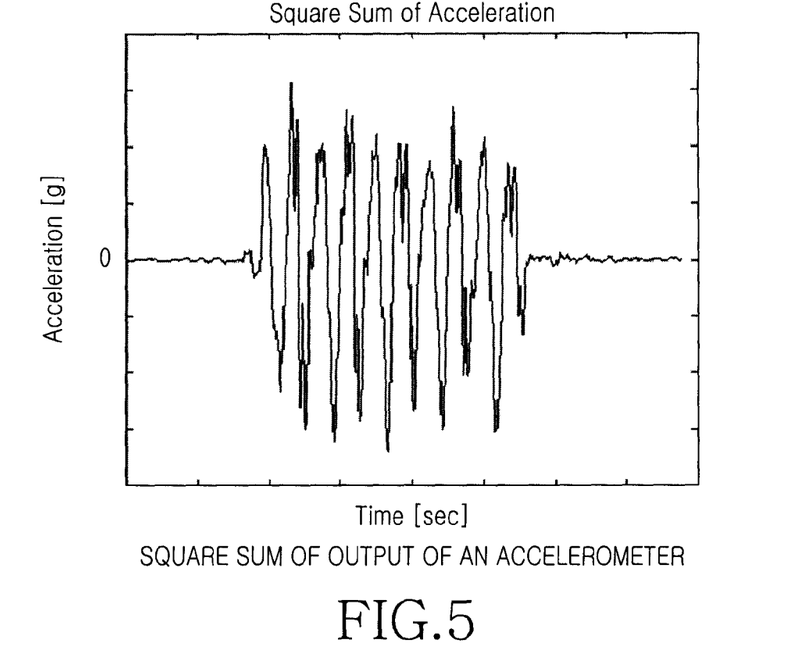
FIG. 5 is a view illustrating a square sum of output signals in axes of an accelerometer in the case in which an exemplary movement distance measuring apparatus of the present invention is located in a pocket of the pants of a pedestrian.
Figure 6:
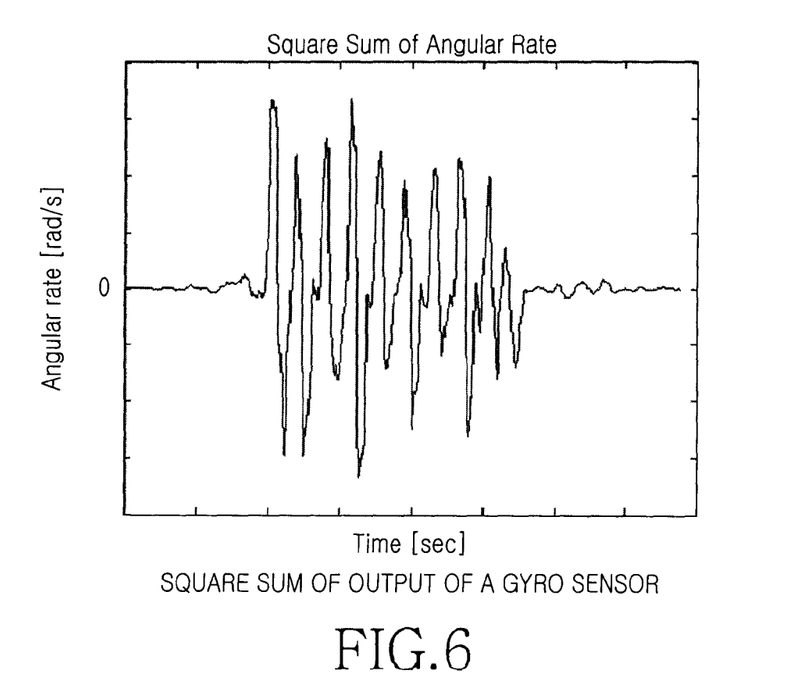
FIG. 6 is a view illustrating a square sum of output signals in axes of a gyro sensor in the case in which an exemplary movement distance measuring apparatus of the present invention is located in a pocket of the pants of a pedestrian.

That is, the step detection unit 32 removes noise and errors by squaring the outputs of the axes, which are output from the accelerometer 20, and summating the resultant square values. The step detection unit 32 outputs the result as illustrated in FIG. 5. Further, the step detection unit 32 removes noise and errors by squaring the Outputs of the axes, which are output from the gyro sensor 40 and summating the resultant square values. The step detection unit 32 outputs that result as illustrated in FIG. 6. Then, as mentioned above, since it is difficult to detect a step of a pedestrian from the output of the gyro sensor in the case in which the movement distance measuring apparatus 30 is mounted at the waist of the pedestrian, the wave forms in FIGS. 5 and 6 are those obtained in the case in which the movement distance measuring apparatus 30 is mounted in a pocket.

Figure 7:
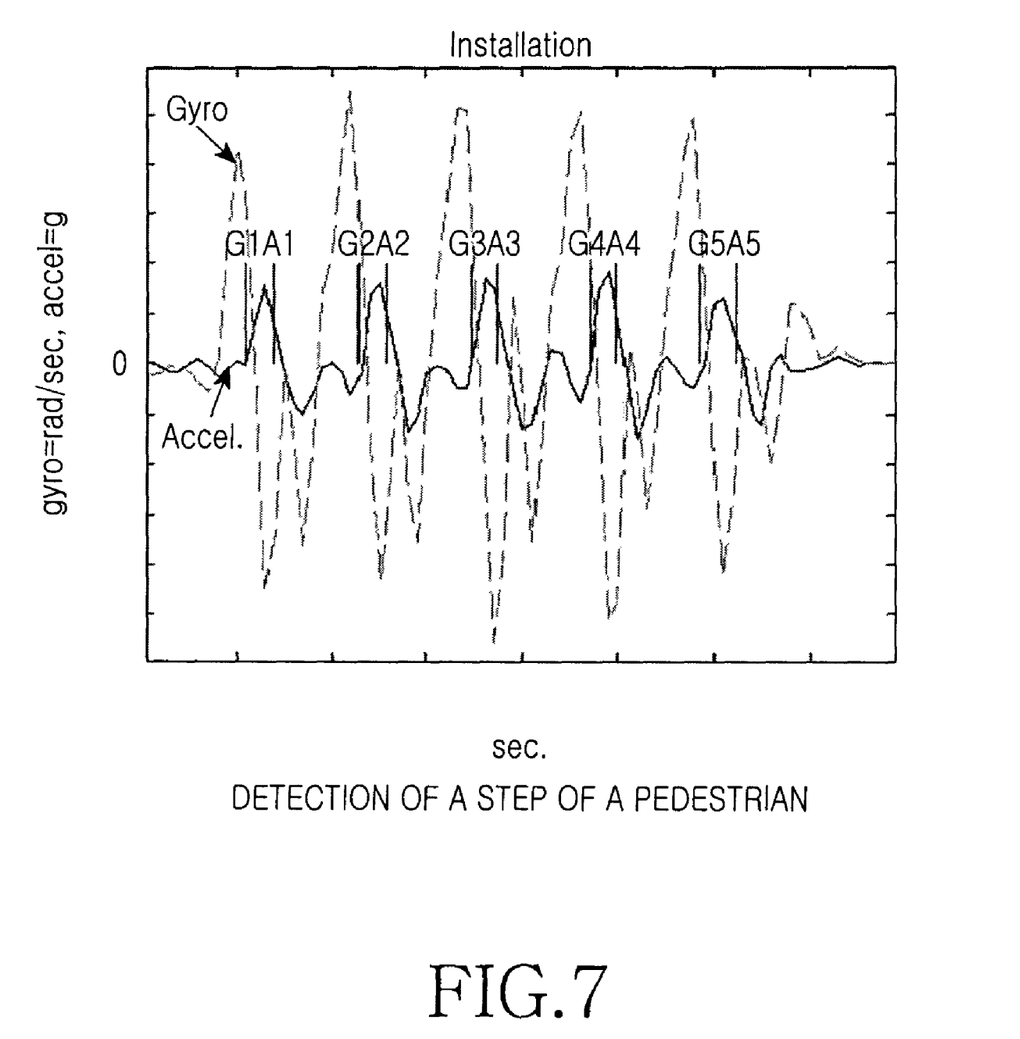
FIG. 7 is a view illustrating wave forms according to detection of a step of a pedestrian using an exemplary accelerometer and gyro sensor of the present invention.

The step detection unit 32 can detect a step using the acceleration signal and an angular speed signal which have been measured in the above-mentioned exemplary method. FIG. 7 is a view illustrating waves of an output signal of the accelerometer 20 and an output signal of the gyro sensor 40 in the case in which the step detection unit 32 detects a step of a pedestrian. In FIG. 7, the reference numerals G1 to G5 represent steps detected by output signals of the gyro sensor 40 and the reference numerals A1 to A5 represent steps detected by output signals of the accelerometer 20.

Consequently, a step of a pedestrian can be detected using the accelerometer 20 in both cases in which the accelerometer is mounted at the waist of the pedestrian or is located in a pocket of the pedestrian. However, the detection of a step using the gyro sensor 40 is possible only when the portable terminal is located in a pocket. This is because rotation rarely appears in the case in which the gyro sensor 40 is mounted at the waist of a pedestrian. However, rotation typically does appear, for example by the movement of a thigh in the case in which the gyro sensor 40 is located in a pocket of the pants of the pedestrian, and can be detected by the gyro sensor 40.

Further, in the case in which the portable terminal is located in a user's pocket, it can be seen that the detection of a step by the gyro sensor 40 is done before the detection of the step by the accelerometer 20.

The step detection unit 32 provides the step detection result to the mounting position determination unit 34. The mounting position determination unit 34 determines whether the portable terminal is mounted at the waist of a pedestrian or is located in a pocket on the basis of a step detection result from the step detection unit 32. More particularly, the mounting position determination unit 34 determines that the portable terminal is located in a pocket of a pedestrian if a step is detected on the basis of an output signal of the accelerometer 20 and is detected on the basis of an output signal of the gyro sensor. Further, the mounting position determination unit 34 determines that the portable terminal is mounted at the waist of a pedestrian if a step is detected on the basis of an output signal of the accelerometer 20 and is not detected on the basis of an output signal of the gyro sensor 40. Further, the mounting position determination unit 34 outputs the mounting position determination result to the step length estimation unit 36. The step length estimation unit 36 determines whether the portable terminal is mounted at the waist of a pedestrian or is located in a pocket, and estimates a step length using a different step length estimation parameter coefficient according to the mounting position of the movement distance measuring apparatus.

Figure 8:
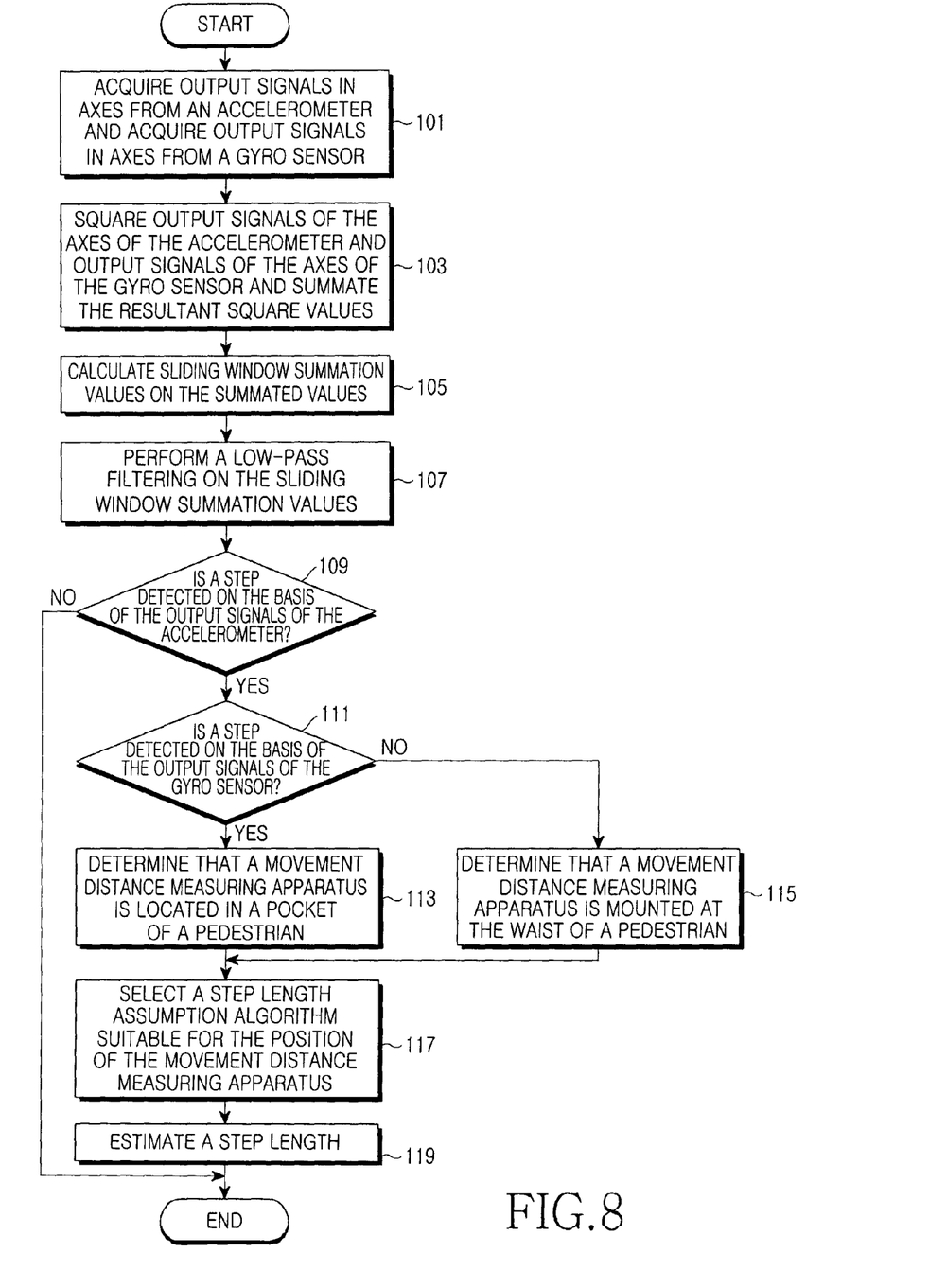
FIG. 8 is a flow chart illustrating a method in which a movement distance measuring apparatus according to an exemplary embodiment of the present invention uses a different step length estimation parameter coefficient according to a mounting position.

FIG. 8 is a flow chart illustrating a method in which a movement distance measuring apparatus according to an exemplary embodiment of the present invention uses a different step length estimation parameter coefficient according to a mounting position.

Referring to FIG. 8, in step 101 the movement distance measuring apparatus 30 acquires output signals of the axes from the accelerometer 20 and acquires output signal o the axes from the gyro sensor 40. In step 103, the movement distance measuring apparatus 30 squares the output signals of the axes of the accelerometer 20 and summates the resultant square values, and squares the output signals of the axes of the gyro sensor 40 and summates the resultant square values. As mentioned above, since the mounting position of the portable terminal is not fixed, the output signals of the sensors are squared and the resultant square values are then summated to remove the directionality of the output signals.

The acceleration signals and the angular speed signals of the axes which are output from the accelerometer 20 and the gyro sensor 40 contain various errors as well as noise. For example, in an exemplary embodiment in which the accelerometer 20 and the gyro sensor 40 are mounted to a hand-held apparatus such as a portable terminal, since the axes of the accelerometer 20 and the gyro sensor 40 are not accurately fixed and may be shaken, noise, biases, conversion coefficient errors, and non-arrangement errors may be generated more severely. In this way, noise, biases, and various errors included in the acceleration signals influence the detection of a step pattern, obstructing accurate detection of a step.

Therefore, a movement distance measurement unit 120 according to an exemplary embodiment of the present invention performs a sliding window summation with respect to the summed value in step 105, and removes the noise included in the summation value.

However, even if the sliding window summation is performed, the noise included in the acceleration signal and the angular speed signal are removed but biases and various errors, such as conversion coefficient errors and non-arrangement errors, are not removed. Therefore, the calculated sliding window summation value may still include a bias and various error components.

Accordingly, the movement distance measuring apparatus 30 removes biases and errors included in the sliding window summation value by performing a low-pass filtering on the sliding window summation value in step 107. That is, the sliding window summation value is signal-processed sufficiently enough to represent a step pattern.

Thereafter, the movement distance measuring apparatus 30 determines whether a step is detected on the basis of the sliding window summation data calculated from the output signals of the accelerometer in step 109. If a step is detected, the movement distance measuring apparatus 30 proceeds to step 111 to determine if a step is detected on the basis of the sliding window summation data calculated from the output signals of the gyro sensor 40. If a step is detected on the basis of the output signals of the gyro sensor 40, the movement distance measuring apparatus 30 proceeds to step 113 to determine that the movement distance measuring apparatus is located in a pocket of a pedestrian. If a step is not detected on the basis of the output signals of the gyro sensor 40 in step 111, the movement distance measuring apparatus 30 determines that the movement distance measuring apparatus is mounted at the waist of the pedestrian in step 115.

The movement distance measuring apparatus 30 recognizes the determined position and selects a step length estimation algorithm suitable for the position determined in step 117. That is, the movement distance measuring apparatus 30 determines whether it is mounted at the waist of a pedestrian or is located in a pocket and selects a step length estimation parameter coefficient suitable for the mounting position of the movement distance measuring apparatus 30. Thereafter, the movement distance measuring apparatus 30 estimates a step length using the step length estimation parameter coefficient suitable for the mounting position of the movement distance measuring apparatus in step 119.

The determination of the mounting position of the movement distance measuring apparatus according to whether a step is detected on the basis of the output signal of the gyro sensor is 98 percent accurate in slow walking and 99 percent accurate in normal fast walking, in the case in which the step detection efficiencies of the gyro sensor are secured. It does not represent an average step detection accuracy but represents the worst case. Therefore, it is possible to determine whether the movement distance measuring apparatus is mounted at the waist of a pedestrian or is located in a pocket according to whether a step is detected on the basis of the output signals of the gyro sensor. The mounting position determining efficiency of the present invention is at least 98 percent based on an efficiency test result.

While the invention has been shown and described with reference to certain exemplary embodiments thereof, it will be understood by those skilled in the art that various changes in form and details may be made therein without departing from the spirit and scope of the invention as defined by the appended claims and their equivalents

What is claimed is:

1. A movement distance measuring apparatus comprising:
   an accelerometer for detecting and outputting an acceleration signal of at least one axis;
   a gyro sensor for detecting and outputting an angular speed signal of at least one axis;
   a step detection unit for detecting a step on the basis of the acceleration signal and the angular speed signal;
   a mounting position determination unit for determining a mounting position of the movement distance measuring apparatus, in which the mounting position determination unit determines that the mounting position is a pocket of a user if the step is detected on the basis of both the acceleration signal and the angular speed signal and determines that the mounting position is the waist of the user if the step is detected on the basis of only the acceleration signal; and
   a step length estimation unit for determining a step length by using a step length estimation algorithm that is different according to the mounting position of the movement distance measuring apparatus.

2. A movement distance measuring apparatus according to claim 1, wherein the step detection unit detects the step after squaring the acceleration signal of at least one axis of the accelerometer, summating the resultant square value and performing a sliding window summation and a low-pass filtering on the summation value.

3. A movement distance measuring apparatus according to claim 1, wherein the step detection unit detects the step after squaring the angular speed signal of at least one axis of the gyro sensor, summating the resultant square value and performing a sliding window summation and a low-pass filtering on the summation value.

4. A movement distance measuring apparatus according to claim 1, wherein the movement distance measuring apparatus is mounted to a portable terminal.

5. A movement distance measuring apparatus according to claim 1, wherein the step length estimation unit uses a step length estimation parameter coefficient that is different according to the mounting position of the movement distance measuring apparatus.

6. A method for measuring a movement distance of a movement distance measuring apparatus, the method comprising:
   determining whether a step is detected on the basis of an acceleration signal outputted from an accelerometer and an angular speed signal outputted from a gyro sensor;
   determining that a location of the movement distance measuring apparatus is a pocket of a user if the step is detected on the basis of both the acceleration signal and the angular speed signal and determining that the location thereof is the waist of the user if the step is detected on the basis of only the acceleration signal; and
   using a step length estimation algorithm that is different according to the location of the movement distance measuring apparatus.

7. A movement distance measuring method according to claim 6, wherein the determining of whether the step is detected comprises:
   squaring an output signal on at least one axis of the accelerometer and summating a resultant square value;
   performing a sliding window summation and a low-pass filtering on the summation value; and
   detecting the step.

8. A movement distance measuring method according to claim 6, wherein the determining of whether the step is detected comprises:
   squaring an output signal on at least one axis of the gyro sensor and summating a resultant square value;
   performing a sliding window summation and a low-pass filtering on the summation value; and
   detecting the step.

9. A movement distance measuring method according to claim 6, wherein using the step length estimation algorithm comprises using a step length estimation parameter coefficient that is different according to the location of the movement distance measuring apparatus.

* * * * *